United States Patent
Vemuri et al.

(10) Patent No.: US 6,641,063 B2
(45) Date of Patent: Nov. 4, 2003

(54) MILLING PROCESS FOR THE PRODUCTION OF FINELY MILLED MEDICINAL SUBSTANCES

(75) Inventors: Narasimha M. Vemuri, West Malling (GB); Andrew B. Brown, West Malling (GB); Jean-Rene Authelin, Saint Germain les Arpajon (FR); Patrik Hosek, Kronberg im Taunus (DE)

(73) Assignee: Aventis Pharma Limited, West-Malling (GB)

( * ) Notice: Subject to any disclaimer, the term of this patent is extended or adjusted under 35 U.S.C. 154(b) by 0 days.

(21) Appl. No.: 09/873,161

(22) Filed: Jun. 1, 2001

(65) Prior Publication Data

US 2002/0109025 A1 Aug. 15, 2002

Related U.S. Application Data

(63) Continuation of application No. PCT/GB99/04041, filed on Dec. 1, 1999.

(30) Foreign Application Priority Data

Dec. 1, 1998 (GB) .............................................. 9826284

(51) Int. Cl.$^7$ .......................... B02C 19/06; B02C 19/12
(52) U.S. Cl. .......................................................... 241/5
(58) Field of Search ................................ 241/5, 39, 40; 424/46

(56) References Cited

U.S. PATENT DOCUMENTS

| | | | | |
|---|---|---|---|---|
| 3,937,405 A | * | 2/1976 | Stephanoff | 241/39 |
| 4,767,612 A | | 8/1988 | Hagen et al. | |
| 5,562,923 A | | 10/1996 | Trofast et al. | |
| 5,637,620 A | | 6/1997 | Trofast et al. | |
| 5,817,028 A | * | 10/1998 | Anderson | |

FOREIGN PATENT DOCUMENTS

| | | |
|---|---|---|
| GB | 2273671 | 6/1994 |
| WO | 9631221 | 10/1996 |
| WO | 9831352 | 7/1998 |
| WO | 9954048 | 10/1999 |

OTHER PUBLICATIONS

Jet Pulverizer, Mining Journal, vol. 268, No. 6869, Apr. 14, 1967, p. 275.*

* cited by examiner

Primary Examiner—Mark Rosaenbaum
(74) Attorney, Agent, or Firm—Peter L. Dolan

(57) ABSTRACT

The invention is an improved method of generating fine medicament powders suitable for inhalation. A fluid energy mill is used with conventional milling fluids such as air or nitrogen. The milling fluid is treated to have a controlled relative humidity of between 30% and 70%. This produces a fine medicament powder with a median particle size below 10 micrometer but with little or no amorphous content generated during milling. Scale formation in the mill chamber is also greatly reduced.

12 Claims, No Drawings

MILLING PROCESS FOR THE PRODUCTION OF FINELY MILLED MEDICINAL SUBSTANCES

This application is a continuation of International Application No. PCT/GB99/04041, filed Dec. 1, 1999, incorporated herein by reference.

The present invention relates to a process for the production of finely milled medicinal substances intended for use as inhalation medicaments. Inhalation medicaments must have a fine particle size in order to penetrate deep into the lungs where they can be absorbed. Typically particles less than 10 μm (microns) in size are required. Such fine particles are normally prepared by milling the material to be inhaled. It is well known that the intensive milling required to produce these fine particle sizes can produce profound changes in the crystal structure of the material being milled. The exact changes are governed by the nature of the starting material but commonly freshly milled powders have a greatly increased content of amorphous phase. This initially forms on the surface of the particles but can constitute a large proportion of the total weight of the powder.

Changes in crystal structure, including increase in amorphous content, can cause a number of problems. The particles tend to stick together, making the freshly milled powder extremely cohesive. With time, often under the influence of ambient moisture, the surface phase tends to revert to its more stable original phase. This can cause the particles to be welded together. Furthermore, the crystal form of a pharmaceutical substance can have a significant effect on its potency, as discussed by J. I. Wells in Pharmaceutical Preformulation: The Physiochemical Properties of Drug Substances, John Wiley & Sons, New York (1988). We have now found that by careful control of the milling conditions used we can achieve the required particle size for an inhalation medicament without generating amorphous phases on the surface of the powder.

U.S. Pat. No. 4,767,612 discloses the preparation of triamcinolone acetonide of which 90–95% is in the particle size range of 1 to 5 μm by micronizing in a fluid energy mill.

U.S. Pat. No. 5,562,923 describes a method for producing finely milled highly crystalline medicinal substances intended for use as inhalation medicaments by drying the milled medicament, treating with a non aqueous solvent and then drying. U.S. Pat. No. 5,637,620 uses a different method; the milled medicament is conditioned under controlled conditions of temperature and humidity before being dried. We have now discovered a process which removes the need for such post milling treatments.

In a fluid energy mill the material to be milled is entrained in an air stream and the particles to caused to collide with one another by turbulence in the air stream. In normal operation care is taken to use dry gas as the milling medium. Steam has been used as the milling fluid, but in this case the steam is superheated and not allowed to condense. Surprisingly, we have found that by using a relatively high relative humidity environment we can produce a milled product with the same range of particle size and surface area as conventional micronising procedures but comprising substantially no amorphous content. Another surprising advantage is that build up of scale in the mill during milling is much reduced. Less scale is deposited and the scale which is deposited is less hard and easier to remove.

Therefore, according to the present invention there is provided a method for producing fine, highly crystalline material consisting of fluid energy milling of crystalline material at relative humidity of between 30% and 90%.

Preferably, the relative humidity is between 30 and 90%, more preferably between 30 and 70%. Any gaseous fluid which does not react with water vapour may be used as the milling fluid. Two which are particularly suitable are nitrogen and air.

The milling process may be applied to any crystalline material. However, it is particularly advantageous when used to mill medicament powders, especially medicament powders intended for administration by inhalation.

The particle size of the product is controlled in the conventional manner by adjusting pressure and flow rate of the milling fluid and feed rate of the material to be milled. Any equipment conventionally used in combination with a fluid energy mill to help control product particle size distribution can also be used in conjunction with the claimed method. The reduced tendency to form scale is particularly advantageous when a classifier is used in conjunction with the mill.

The amount of amorphous material in a sample of milled powder can be assessed in a number of ways. Differential Scanning Calorimetry (DSC) will show the heat of crystallisation in a sample containing amorphous material. Alternatively the change in weight of a sample exposed to an atmosphere of controlled temperature and humidity can give a measure of the change in amorphous content. In both methods the apparatus is calibrated using samples of known crystalline content and the unknown sample measured by comparing the magnitude of the measurement for the unknown with the known samples.

Also, amorphous substances usually have a substantially higher specific surface area than the corresponding crystalline substance. Thus, when a powder with an appreciable amorphous content crystallises the specific surface area falls. When a powder produced by conventional milling with a substantial amorphous content is stored in contact with the atmosphere the amorphous material tends to crystallise over a period of time. Within a few days, or weeks at most, surface area falls to a substantially stable value.

Accordingly, in the context of the present invention a powder may be considered to have substantially no amorphous content if its specific surface area does not change substantially when stored in a container open to the atmosphere for a week or more. The change in surface area should preferably be no more than 20% of the initial value, more preferably no more than 10% and most preferably no more than 5%. Alternatively a powder would be considered to have substantially no amorphous content if the level immediately after milling as measured by weight change under controlled relative humidity or DSC is less than 5%, more preferably less than 2% and most preferably less than 1%.

Surface area can be measured by gas absorption using the Brunauer-Emmet-Teller method or by air permeametry using the Blaine method. Results given here relate to the latter method which is described in the standard method of the l'Association Francaise de Normalisation (AFNOR) no P 15–442 March 1987.

Weight change under controlled relative humidity is measured using a DVS 1 dynamic vapour sorption apparatus. A small weighed sample is placed in a microbalance pan and held at constant temperature of 25° C. and a relative humidity of 75%. Weight change is measured as a function of time over a period of at least 5 hours. The plot of weight v time shows a peak which is proportional to the proportion of amorphous material present. The equipment is calibrated with samples of known amorphous content produced by mixing fully crystalline and fully amorphous materials.

DSC measurements were carried out using a Seiko RDC 220 system. The sample is weighed into the measuring pan and held at a temperature below the recrystallisation temperature for 30 minutes under a flow of dry nitrogen to remove any surface moisture. The sample was then heated at a constant rate of 20° C. per minute. The exothermic peak due to recrystallisation is measured. As above the method is calibrated using samples of known amorphous content.

A detailed method of carrying out the process is given. The optimum method of introducing water vapour and controlling relative humidity during milling will depend on the exact design of mill used and the following method is not to be considered limiting.

EXAMPLE

A 10 cm (four inch) diameter pancake mill was used for the experiments. Milling air is introduced to the circumference of the mill and powder to be milled is blown in through a venturi orifice also entering through the circumference of the milling chamber. Milled product, entrained in the milling fluid, exits through a central outlet. The temperature of the milling gas and/or the feed gas can be controlled. Relative humidity within the milling chamber is controlled by adding water vapour to the feed gas after it has expanded out of the venturi orifice. Liquid water is pumped using a metered pump through a vaporiser operating at a temperature greater than 100° C. and the water vapour passed to the venturi outlet. The rate of water addition required is calculated using standard physical principles and is adjusted during milling to reflect changes in milling conditions.

The table below gives results obtained when milling triamcinolone acetonide (TAA) or salbutamol sulphate according to the present invention. The same batch of feed was used for each compound. For each compound the starting material had a median particle size (d50) as measured by Malvern particle size analyser of around 25 $\mu$m (micron). The gas used was nitrogen in all experiments.

Surface area was measured using the Blaine air permeability method. Where samples were stored for ageing trials the samples were kept in a 60% relative humidity atmosphere at 25° C.

Run 1 and Run 2 show the effect of high relative humidity under intensive milling conditions for TAA. Both milling conditions produced similar products in terms of surface area and median particle size, but the amorphous content, as measured by DSC, was more than a factor of ten reduced by using high humidity milling gas (Run 2).

Run 3 and Run 4 also used TAA and show that under less intensive milling conditions the use of humid nitrogen still gives negligible amorphous content whereas dry nitrogen still gives a significant amorphous content.

Run 5 shows that under the gentlest milling conditions the use of dry gas can still give a milled TAA product with low amorphous content.

Run 6 and Run 7 show that the use of high humidity nitrogen gives a significant improvement in mill performance in that a finer TAA product is obtained.

Run 8 and Run 9 show that a relative humidity of 30% is effective in preventing the development of amorphous phase in the TAA product.

Run 10 and Run 11 show that the same effect is obtained when a quite different compound, salbutamol sulphate, is used. Run 10 shows that milling with dry nitrogen generates a significant amorphous content, whereas milling with nitrogen with a 70% relative humidity generated no detectable amorphous material (Run 11).

TAA from Run 4 was tested in an Ultrahaler® device and the results compared with TAA milled in the conventional way. The Ultrahaler® is a dry powder inhaler whose basic operation is described in EP 407 028.

A compact was produced by compressing a mixture of 5% TAA with 95% lactose with a median particle size of 50 micrometer. The compact was loaded into the inhaler and doses cut off from it using a blade. Up to 200 doses can be obtained from each device. The important parameters are dose uniformity and the percentage respirable fraction of TAA produced in each dose.

For TAA produced by conventional means the mean respirable fraction produced was 44%, and 83% of the doses cut were within 20% of their nominal weight. For TAA produced under the conditions of Run 4 the mean respirable fraction was also 44% but the percentage of doses within 20% of nominal weight rose to 95%.

In all experiments using low humidity (Runs 1,3,5) there was a build up of a very hard scale on the inside of the mill. This must be removed periodically by shutting down the mill and chipping the scale away. In contrast the experiments using high relative humidity of 30% and 70% produced less scale. The scale which was produced was much softer and easier to remove. In no case was any sign of condensation seen in the mill chamber or in the product.

| | Run 1 | Run 2 | Run 3 | Run 4 | Run 5 | Run 6 | Run 7 | Run 8 | Run 9 | Run 10 | Run 11 |
|---|---|---|---|---|---|---|---|---|---|---|---|
| Feed Rate (kg/hr) | 0.25 | 0.25 | 0.5 | 0.66 | 1 | 1 | 1 | 1 | 1 | 0.5 | 0.5 |
| Milling Pressure (bar) | 7 | 5 | 7 | 7 | 3 | 3 | 3 | 7 | 3 | 6 | 6 |
| Feed Gas Pressure (bar) | 9 | 9 | 9 | 8 | 4 | 4 | 3 | 8 | 4 | 7 | 7 |
| Relative Humidity (%) | <2 | 70 | <2 | 70 | <2 | 70 | 70 | 30 | 30 | <2 | 70 |
| Product Sw (m2/g) | 1.8 | 1.8 | 2.2 | 2.3 | 0.6 | 1.4 | 1.0 | 2.0 | 1.3 | 2.9 | 3.1 |
| Product Sw (m2/g) after 1 week | | 1.8 | | | | 1.4 | 1.0 | | | | |
| Product Sw (m2/g) after 2 weeks | | | 2.0 | 2.2 | | | | | | | |
| Product Sw (m2/g) after 1 month | | 1.7 | | | | | | | | | |
| Product Sw (m2/g) after 2 months | | 1.7 | | | | | | | | | |
| Product Sw (m2/g) after 3 months | | 1.8 | | | | 1.4 | 1.0 | | | | |
| Product D50 | 2.5 | 2.9 | 2.1 | 1.8 | | 3.7 | 5.1 | 2.7 | 4.1 | 3.0 | 2.7 |
| Product D50 after 1 week | | 2.7 | | | | 3.2 | 5.8 | | | | |
| Product D50 after 2 weeks | | | | | | | | | | | |
| Product D50 after 1 month | | 2.7 | | | | 3.2 | 6.2 | | | | |
| Product D50 after 2 months | | 3.0 | | | | | | | | | |
| Product D50 after 3 months | | 2.9 | | | | | | | | | |

-continued

|  | Run 1 | Run 2 | Run 3 | Run 4 | Run 5 | Run 6 | Run 7 | Run 8 | Run 9 | Run 10 | Run 11 |
|---|---|---|---|---|---|---|---|---|---|---|---|
| Amorphous content (%) | 16.2 | n.d. | 6.5 | n.d. | 0.24 | n.d. | n.d. | n.d. | n.d. | 5.1 | n.d. |
| Amorphous content (%) after 1 week |  | n.d. |  |  |  |  |  |  |  |  |  |
| Amorphous content (%) after 2 weeks | n.d. |  | n.d. |  |  |  |  |  |  |  |  | n.d. = not detected

What is claimed is:

1. A method for producing a fine, highly crystalline material product, the method comprising fluid energy milling a crystalline material at a relative humidity of between 30% and 90%.

2. A method according to claim 1 wherein the relative humidity is between 30% and 70%.

3. A method according to claim 1 wherein the milling fluid is air.

4. A method according to claim 1 wherein the milling fluid is nitrogen.

5. A method according to claim 1 wherein the crystalline material comprises a medicament powder.

6. A method according to claim 5 wherein the crystalline material is triamcinolone acetonide.

7. A method according to claim 5 wherein the crystalline material is salbutamol sulphate.

8. A method according to any claim 1 wherein the product has an amorphous content of less than 5%.

9. A method according to claim 8 wherein the product has an amorphous content of less than 2%.

10. A method according to claim 9 wherein the product has an amorphous content of less than 1%.

11. A method according to claim 1 wherein the product consists of a medicament powder in a form suitable for inhalation.

12. A method according to claim 11 wherein the product has a median particle size of less than 10 $\mu$m.

* * * * *